(12) United States Patent
Atkins et al.

(10) Patent No.: US 12,156,543 B2
(45) Date of Patent: Dec. 3, 2024

(54) VAPORIZABLE MATERIAL INSERT FOR VAPORIZER DEVICE

(71) Applicant: JUUL Labs, Inc., San Francisco, CA (US)

(72) Inventors: Ariel Atkins, San Francisco, CA (US); Ian Garcia-Doty, Oakland, CA (US); Eddie G. Gonzalez, San Francisco, CA (US); Paul R. Vieira, Oakland, CA (US)

(73) Assignee: JUUL Labs, Inc., San Francisco, CA (US)

( * ) Notice: Subject to any disclaimer, the term of this patent is extended or adjusted under 35 U.S.C. 154(b) by 342 days.

(21) Appl. No.: 17/548,123

(22) Filed: Dec. 10, 2021

(65) Prior Publication Data
US 2022/0095685 A1    Mar. 31, 2022

Related U.S. Application Data

(63) Continuation of application No. PCT/US2020/037047, filed on Jun. 10, 2020.
(Continued)

(51) Int. Cl.
*A24F 40/42* (2020.01)
*A24D 3/17* (2020.01)
(Continued)

(52) U.S. Cl.
CPC ............. *A24F 40/485* (2020.01); *A24D 3/17* (2020.01); *A24F 40/10* (2020.01); *A24F 40/20* (2020.01); *A24F 40/42* (2020.01)

(58) Field of Classification Search
CPC ......... A24F 40/485; A24F 40/42; A24F 40/20
See application file for complete search history.

(56) References Cited

U.S. PATENT DOCUMENTS 3,373,915 A    3/1968   Anderson et al.
4,708,151 A   11/1987   Shelar
(Continued)

FOREIGN PATENT DOCUMENTS

CA         3010559  A1     7/2017
CN       102753047  A     10/2012
(Continued)

OTHER PUBLICATIONS

Guo, et al. (Mar. 31, 2016) "Heat Transfer Performance of Atomizer of Electronic Cigar", Popular Science and Technology, 18(3):52-54.

*Primary Examiner* — Neil Abrams
(74) *Attorney, Agent, or Firm* — MINTZ LEVIN COHN FERRIS GLOVSKY AND POPEO, P.C.

(57) ABSTRACT

A vaporization device includes a vaporizer body including a vaporizable material insert receptacle configured to receive a vaporizable material insert including vaporizable material. The vaporizable material insert can include an airflow pathway and an airflow control feature at least partly made out of vaporizable material. Various embodiments of the airflow control feature are described that include one or more features for controlling an amount of heat transferred from heated airflow traveling along the airflow pathway and the vaporizable material of the airflow control feature. Related systems, methods, and articles of manufacture are also described.

20 Claims, 5 Drawing Sheets

Related U.S. Application Data

(60) Provisional application No. 62/860,747, filed on Jun. 12, 2019.

(51) Int. Cl.
*A24F 40/10* (2020.01)
*A24F 40/20* (2020.01)
*A24F 40/485* (2020.01)

(56) References Cited

U.S. PATENT DOCUMENTS

| | | |
|---|---|---|
| 5,042,509 A | 8/1991 | Banerjee et al. |
| 5,065,776 A | 11/1991 | Lawson et al. |
| 5,249,586 A | 10/1993 | Morgan et al. |
| 5,479,948 A | 1/1996 | Counts et al. |
| 7,726,320 B2 | 6/2010 | Robinson et al. |
| 8,490,629 B1 | 7/2013 | Shenassa et al. |
| 8,671,952 B2 | 3/2014 | Winterson et al. |
| 8,869,792 B1 | 10/2014 | Lee |
| 8,991,402 B2 | 3/2015 | Bowen et al. |
| 9,408,416 B2 | 8/2016 | Monsees et al. |
| 9,943,114 B2 | 4/2018 | Batista |
| 10,729,179 B2 * | 8/2020 | Atkins ................. A61M 11/042 |
| 11,129,414 B2 * | 9/2021 | Atkins ................... H05B 3/06 |
| 11,147,128 B2 | 10/2021 | Qiu |
| 11,464,082 B2 | 10/2022 | Jobanputra et al. |
| 2004/0055613 A1 | 3/2004 | Horian |
| 2005/0268911 A1 | 12/2005 | Cross et al. |
| 2006/0032501 A1 | 2/2006 | Hale et al. |
| 2008/0092912 A1 | 4/2008 | Robinson et al. |
| 2009/0126746 A1 | 5/2009 | Strickland et al. |
| 2009/0151717 A1 | 6/2009 | Bowen et al. |
| 2009/0260642 A1 | 10/2009 | Monsees et al. |
| 2010/0024834 A1 | 2/2010 | Oglesby et al. |
| 2011/0041861 A1 | 2/2011 | Sebastian et al. |
| 2011/0226236 A1 | 9/2011 | Buchberger |
| 2011/0290267 A1 | 12/2011 | Yamada et al. |
| 2013/0042865 A1 | 2/2013 | Monsees et al. |
| 2014/0301721 A1 | 10/2014 | Ruscio et al. |
| 2014/0366898 A1 | 12/2014 | Monsees et al. |
| 2015/0272218 A1 | 10/2015 | Chen |
| 2015/0335070 A1 | 11/2015 | Sears et al. |
| 2016/0120225 A1 | 5/2016 | Mishra et al. |
| 2016/0120227 A1 | 5/2016 | Levitz et al. |
| 2016/0309782 A1 | 10/2016 | Malgat et al. |
| 2016/0338412 A1 | 11/2016 | Monsees et al. |
| 2017/0055575 A1 | 3/2017 | Wilke et al. |
| 2017/0055580 A1 | 3/2017 | Blandino et al. |
| 2017/0071250 A1 | 3/2017 | Mironov et al. |
| 2017/0143041 A1 | 5/2017 | Batista et al. |
| 2017/0156403 A1 | 6/2017 | Gill et al. |
| 2017/0164657 A1 | 6/2017 | Batista |
| 2018/0027877 A1 | 2/2018 | Tucker et al. |
| 2018/0084823 A1 | 3/2018 | Fuisz et al. |
| 2018/0110263 A1 | 4/2018 | Borkovec et al. |
| 2018/0132534 A1 | 5/2018 | Reevell |
| 2018/0228216 A1 | 8/2018 | Saygili |
| 2018/0295881 A1 | 10/2018 | Mironov et al. |
| 2019/0001077 A1 | 1/2019 | Xu et al. |
| 2019/0037921 A1 | 2/2019 | Kennedy et al. |
| 2019/0098930 A1 | 4/2019 | Fallon et al. |
| 2019/0124982 A1 * | 5/2019 | Atkins ................... A24F 40/30 |
| 2019/0166913 A1 | 6/2019 | Trzecieski |
| 2019/0200674 A1 | 7/2019 | Tucker et al. |
| 2019/0208827 A1 | 7/2019 | Mironov et al. |
| 2020/0107585 A1 * | 4/2020 | Atkins ................... H05B 3/42 |
| 2020/0113245 A1 | 4/2020 | Rosser et al. |
| 2020/0120993 A1 * | 4/2020 | Atkins ................... H05B 3/03 |
| 2021/0386120 A1 | 12/2021 | Gill |
| 2022/0046997 A1 * | 2/2022 | Atkins ................... A24F 40/51 |
| 2022/0095685 A1 * | 3/2022 | Atkins ................. A61M 11/042 |
| 2022/0151285 A1 * | 5/2022 | Garcia-Doty ........... A24F 40/42 |
| 2022/0160040 A1 | 5/2022 | Zhang et al. |
| 2023/0309615 A1 * | 10/2023 | Mauchle .................. A24F 7/00 |
| | | 131/329 |

FOREIGN PATENT DOCUMENTS

| | | |
|---|---|---|
| CN | 103783674 A | 5/2014 |
| CN | 105764367 A | 7/2016 |
| CN | 106572705 A | 4/2017 |
| CN | 106659247 A | 5/2017 |
| CN | 106659250 A | 5/2017 |
| CN | 106858726 A | 6/2017 |
| CN | 107772540 A | 3/2018 |
| CN | 111432670 A | 7/2020 |
| CN | 113163855 A | 7/2021 |
| EP | 2394520 A1 | 12/2011 |
| EP | 3420829 A1 | 1/2019 |
| EP | 3664631 A2 | 6/2020 |
| EP | 3795009 A1 | 3/2021 |
| GB | 2527597 A | 12/2015 |
| GB | 2547699 A | 8/2017 |
| GB | 2568411 B | 8/2019 |
| JP | 2001-507576 A | 6/2001 |
| JP | 2010506594 A | 3/2010 |
| JP | 2010517568 A | 5/2010 |
| JP | 2010178730 A | 8/2010 |
| JP | 2015-509709 A | 4/2015 |
| JP | 2016538850 A | 12/2016 |
| JP | 2017018146 A | 1/2017 |
| JP | 2017-529896 A | 10/2017 |
| JP | 2020536536 A | 12/2020 |
| KR | 20-2012-0008751 U | 12/2012 |
| KR | 10-2016-0112769 A | 9/2016 |
| KR | 10-2021-0155091 A | 12/2021 |
| RU | 2602053 C2 | 11/2016 |
| RU | 2604313 C2 | 12/2016 |
| RU | 2629878 C1 | 9/2017 |
| RU | 2655239 C2 | 5/2018 |
| WO | WO-2006120570 A2 | 11/2006 |
| WO | WO-2011079932 A1 | 7/2011 |
| WO | WO-2015082651 A1 | 6/2015 |
| WO | WO-2015179388 A1 | 11/2015 |
| WO | WO-2016005533 A1 | 1/2016 |
| WO | WO-2016062777 A1 | 4/2016 |
| WO | WO-2016079589 A1 | 5/2016 |
| WO | WO-2016162446 A1 | 10/2016 |
| WO | WO-2017072148 A1 | 5/2017 |
| WO | WO-2017122196 A1 | 7/2017 |
| WO | WO-2017129617 A1 | 8/2017 |
| WO | WO-2017207418 A1 | 12/2017 |
| WO | WO-2017207419 A1 | 12/2017 |
| WO | WO-2017207582 A1 | 12/2017 |
| WO | WO-2018019578 A1 | 2/2018 |
| WO | WO-2018122389 A1 | 7/2018 |
| WO | WO-2018122978 A1 | 7/2018 |
| WO | WO-2018206615 A2 | 11/2018 |
| WO | WO-2019057942 A1 | 3/2019 |
| WO | WO-2019073237 A1 | 4/2019 |
| WO | WO-2019122015 A1 | 6/2019 |
| WO | WO-2020028591 A1 | 2/2020 |
| WO | WO-2020239599 A1 | 12/2020 |

* cited by examiner

VAPORIZABLE MATERIAL INSERT FOR VAPORIZER DEVICE

CROSS-REFERENCE TO RELATED APPLICATION

This application is a bypass continuation and claims priority to PCT/US20/37047, filed on Jun. 10, 2020 and entitled "Vaporizable Material Insert for Vaporizer Device" which claims priority under 35 U.S.C. § 119(a) to U.S. Provisional application Ser. No. 62/860,747, filed on Jun. 12, 2019 and entitled "VAPORIZABLE MATERIAL INSERT FOR VAPORIZER DEVICE," the disclosures of which are incorporated by reference herein in their entirety.

TECHNICAL FIELD

The subject matter described herein relates to various embodiments of a vaporizable material insert for use with a vaporizer device.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking. Vaporizers are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes a vaporizable material, for example, by causing the vaporizable material to transition at least partially to a gas phase. The vaporizable material may be a liquid, a solution, a solid, a paste, a wax, and/or any other form compatible for use with a specific vaporizer device. Moreover, the vaporizable material used with a vaporizer can be provided within a vaporizer cartridge, which may be a separable part of the vaporizer device that contains the vaporizable material and having an outlet (e.g., a mouthpiece) for delivering the aerosol generated by the vaporization of the vaporizable material to a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated when the vaporized vaporizable material is combined with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporization device.

In some embodiments, vaporizer cartridges configured to heat solid vaporizable material (e.g. plant material such as tobacco leaves and/or parts of tobacco leaves) can require higher temperatures for inner tobacco regions to reach a minimum required temperature for vaporization. As a result, burning the solid vaporizable material at these high peak temperatures can produce toxic byproducts (e.g., chemical elements or chemical compounds).

Vaporizer devices can be categorized into two classes, those that heat through conduction and those that heat through convection. For example, conduction-based vaporizer devices may be configured to vaporize liquid vaporizable material using a heating element contacting the liquid vaporizable material. As such, the liquid vaporizable material may contaminate the heating element, which can compromise performance of the vaporizer device. Some vaporizers may incorporate the heating element into the disposable part of the vaporizer device (e.g., the cartridge), such that the heating element may be replaced with each new cartridge and thereby limit, but not eliminate, heating element contamination. However, this can increase manufacturing labor and costs associated with the disposable. Furthermore, uniform heating of the vaporizable material in current conduction-based vaporizers may be difficult to achieve due to the low thermal conductivity of certain vaporizable materials (e.g., plant materials, such as tobacco).

Convection-based vaporizers may also present a challenge in uniformly heating the vaporizable material, particularly solid vaporizable material. For example, as hot air flows through the reservoir, a temperature gradient may develop along the vaporizable material. In conventional convection-based systems, upstream portions of the vaporizable material (e.g., portions located closer to the heater) may be heated to a higher temperature than portions of the vaporizable material that are located further downstream (e.g., closer to the user/air outlet). If the upstream portions of the vaporizable material become too hot, then the vaporizable material may char and/or burn, resulting in an unpleasant taste and/or release of undesirable byproducts. If, on the other hand, the vaporizer temperature is kept low enough to ensure that the vaporizable material does not char or burn, then portions of the vaporizable material that are downstream may not be fully vaporized, which may result in a waste of materials and/or decreased vapor production. Additionally, because the vaporizable material may change shape while drying, the path along which hot air flows through the material may be altered, causing uneven and/or unpredictable heating and further exacerbating the issues noted above.

SUMMARY

In certain aspects of the current subject matter, challenges associated with efficiently and effectively forming an inhalable aerosol from vaporizable material can be addressed by inclusion of one or more of the features described herein or comparable/equivalent approaches as would be understood by one of ordinary skill in the art. Aspects of the current subject matter relate to methods and system associated with a vaporizable material insert for inserting in a vaporizer device to form an inhalable aerosol.

In one aspect, a vaporizable material insert is described for use with a vaporizer device to form an inhalable aerosol.

The vaporizable material insert can include a housing including an inlet and an outlet. The vaporizable material insert can include an airflow control feature comprising a vaporizable material, and the airflow control feature can extend between the inlet and the outlet of the housing. The vaporizable material insert can further include an airflow pathway extending between the inlet and the outlet of the housing and at least partly formed by the airflow control feature. The airflow pathway can allow a heated airflow to travel therealong and include an upstream section and a downstream section. The upstream section can include a first airflow pathway characteristic that controls a first airflow characteristic of the heated airflow for achieving a first amount of heat transfer between the heated airflow at a first temperature and the vaporizable material along the upstream section. The downstream section can include a second airflow pathway characteristic that controls a second airflow characteristic of the heated airflow for achieving a second amount of heat transfer between the heated airflow at a second temperature and the vaporizable material along the downstream section. The first temperature can be higher than the second temperature, and the first amount of heat transfer can be approximately the same as the second amount of heat transfer.

In some variations one or more of the following features can optionally be included in any feasible combination. For example, the first airflow pathway characteristic and the second airflow pathway characteristic can each include a diameter, a cross-section area, a shape, or a length of the upstream section and the downstream section, respectively. The first airflow pathway characteristic can be different than the second airflow pathway characteristic. The first airflow characteristic and the second airflow characteristic can each comprise an airflow rate, an airflow resistance, an airflow pressure, or an airflow travel length. The first airflow characteristic can be different than the second airflow characteristic.

In some embodiments, the upstream section can include a single airflow pathway and the downstream section can include a plurality of secondary pathways. The single airflow pathway can be in fluid communication with each secondary pathway included in the plurality of secondary pathways. In some embodiments, the plurality of secondary pathways can extend in a helical shape along the airflow control feature. The airflow pathway can include a diameter that decreases along the airflow pathway between the inlet and the outlet of the housing.

In some embodiments, the upstream section of the airflow pathway can be formed by a first part of the airflow control feature and the downstream section of the airflow pathway can be formed by a second part of the airflow control feature. The first part can have a different shape than the second part. For example, the first part can form a ring shape and the second part can form a cross shape.

In some embodiments, the vaporizable material includes a solid vaporizable material. The airflow control feature can include a porous substrate containing liquid vaporizable material. In some embodiments, the vaporizable material insert further includes a cooling filter positioned adjacent the outlet of the housing for reducing a temperature of the inhalable aerosol prior to inhalation by a user.

In another aspect, a system for generating an inhalable aerosol is described. The system can include a vaporizable material insert that includes a housing including an inlet and an outlet. The vaporizable material insert can include an airflow control feature comprising a vaporizable material, and the airflow control feature can extend between the inlet and the outlet of the housing. The vaporizable material insert can further include an airflow pathway extending between the inlet and the outlet of the housing and at least partly formed by the airflow control feature. The airflow pathway can allow a heated airflow to travel therealong and include an upstream section and a downstream section. The upstream section can include a first airflow pathway characteristic that controls a first airflow characteristic of the heated airflow for achieving a first amount of heat transfer between the heated airflow at a first temperature and the vaporizable material along the upstream section. The downstream section can include a second airflow pathway characteristic that controls a second airflow characteristic of the heated airflow for achieving a second amount of heat transfer between the heated airflow at a second temperature and the vaporizable material along the downstream section. The first temperature can be higher than the second temperature, and the first amount of heat transfer can be approximately the same as the second amount of heat transfer. The system can further include a vaporizer device including a vaporizable material insert receptacle configured to receive the vaporizable material insert. The vaporizer device of the system can further include a heating element configured to heat airflow upstream from the vaporizable material insert for allowing heated airflow to travel along the airflow pathway of the vaporizable material insert and generate the inhalable aerosol.

In some variations one or more of the following features can optionally be included in any feasible combination of the system. For example, the first airflow pathway characteristic and the second airflow pathway characteristic can each include a diameter, a cross-section area, a shape, or a length of the upstream section and the downstream section, respectively. The first airflow pathway characteristic can be different than the second airflow pathway characteristic. The first airflow characteristic and the second airflow characteristic can each include an airflow rate, an airflow resistance, an airflow pressure, or an airflow travel length. The first airflow characteristic can be different than the second airflow characteristic.

In some embodiments, the upstream section can include a single airflow pathway and the downstream section can include a plurality of secondary pathways. The single airflow pathway can be in fluid communication with each secondary pathway included in the plurality of secondary pathways. In some embodiments, the plurality of secondary pathways can extend in a helical shape along the airflow control feature. The airflow pathway can include a diameter that decreases along the airflow pathway between the inlet and the outlet of the housing.

In some embodiments, the upstream section of the airflow pathway can be formed by a first part of the airflow control feature and the downstream section of the airflow pathway can be formed by a second part of the airflow control feature. The first part can have a different shape than the second part. For example, the first part can form a ring shape and the second part can form a cross shape.

In some embodiments, the vaporizable material includes a solid vaporizable material. The airflow control feature can include a porous substrate containing liquid vaporizable material. In some embodiments, the vaporizable material insert further includes a cooling filter positioned adjacent the outlet of the housing for reducing a temperature of the inhalable aerosol prior to inhalation by a user.

In another interrelated aspect of the current subject matter, a method for generating an inhalable aerosol for inhalation by a user includes receiving a vaporizable material insert into a compartment of a vaporizer device. The vaporizable material insert can include a housing including an inlet and an outlet. The vaporizable material insert can include an airflow control feature comprising a vaporizable material, and the airflow control feature can extend between the inlet and the outlet of the housing. The vaporizable material insert can further include an airflow pathway extending between the inlet and the outlet of the housing and at least partly formed by the airflow control feature. The airflow pathway can allow a heated airflow to travel therealong and include an upstream section and a downstream section. The upstream section can include a first airflow pathway characteristic that controls a first airflow characteristic of the heated airflow for achieving a first amount of heat transfer between the heated airflow at a first temperature and the vaporizable material along the upstream section. The downstream section can include a second airflow pathway characteristic that controls a second airflow characteristic of the heated airflow for achieving a second amount of heat transfer between the heated airflow at a second temperature and the vaporizable material along the downstream section. The first temperature can be higher than the second temperature, and the first amount of heat transfer can be approximately the same as the second amount of heat transfer. The method can further include activating a heating element configured to heat airflow upstream from the vaporizable material insert and forming, as a result of the heated airflow traveling along the airflow pathway of the vaporizable material insert, the inhalable aerosol.

In some variations one or more of the following features can optionally be included in any feasible combination. For example, the first airflow pathway characteristic and the second airflow pathway characteristic can each include a diameter, a cross-section area, a shape, or a length of the upstream section and the downstream section, respectively. The first airflow pathway characteristic can be different than the second airflow pathway characteristic. The first airflow characteristic and the second airflow characteristic can each comprise an airflow rate, an airflow resistance, an airflow pressure, or an airflow travel length. The first airflow characteristic can be different than the second airflow characteristic.

In some embodiments, the upstream section can include a single airflow pathway and the downstream section can include a plurality of secondary pathways. The single airflow pathway can be in fluid communication with each secondary pathway included in the plurality of secondary pathways. In some embodiments, the plurality of secondary pathways can extend in a helical shape along the airflow control feature. The airflow pathway can include a diameter that decreases along the airflow pathway between the inlet and the outlet of the housing.

In some embodiments, the upstream section of the airflow pathway can be formed by a first part of the airflow control feature and the downstream section of the airflow pathway can be formed by a second part of the airflow control feature. The first part can have a different shape than the second part. For example, the first part can form a ring shape and the second part can form a cross shape.

In some embodiments, the vaporizable material includes a solid vaporizable material. The airflow control feature can include a porous substrate containing liquid vaporizable material. In some embodiments, the vaporizable material insert further includes a cooling filter positioned adjacent the outlet of the housing for reducing a temperature of the inhalable aerosol prior to inhalation by a user.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
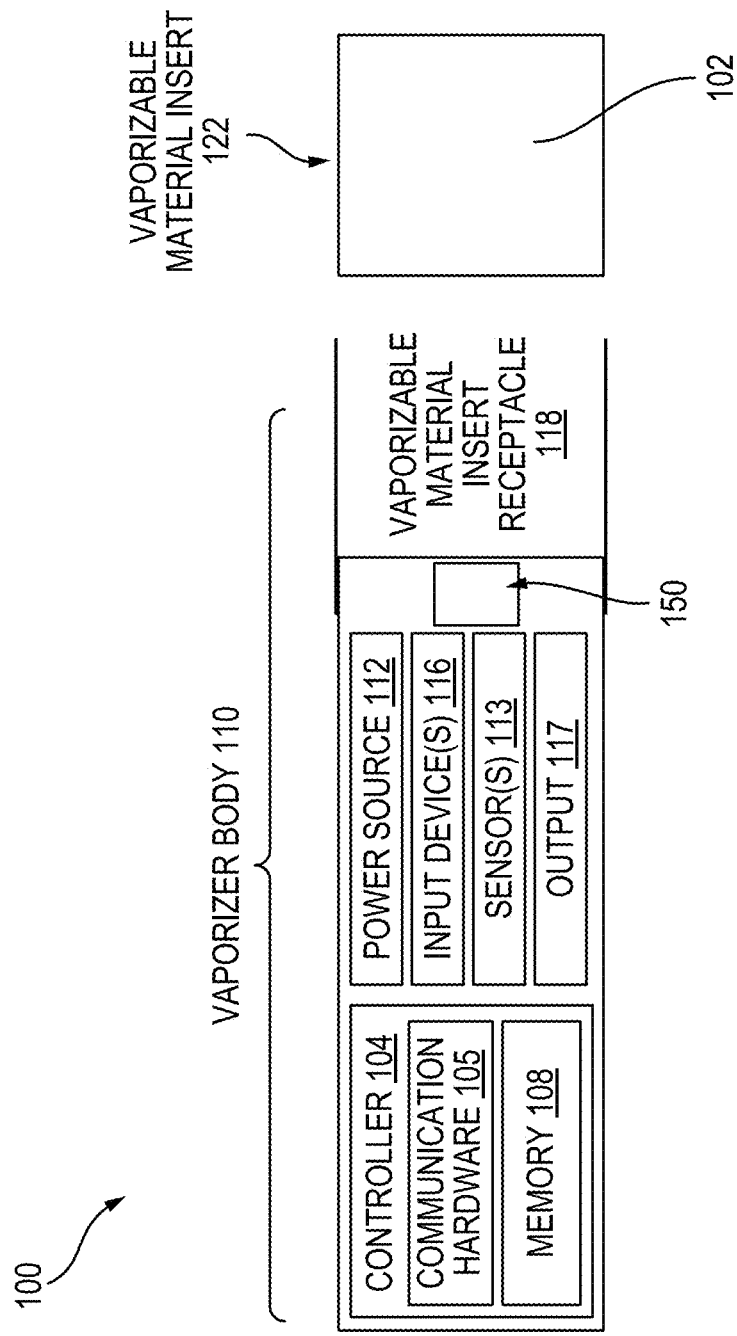
FIG. 1 illustrates a block diagram of a vaporizer consistent with implementations of the current subject matter.

Implementations of the current subject matter include devices and methods relating to vaporizing of one or more materials for inhalation by a user. For example, various embodiments of a vaporizer cartridge or vaporizable material insert for use with a vaporizer device are described herein. The term "vaporizer device" as used in the following description and claims refers to any of a self-contained apparatus, an apparatus that includes two or more separable parts (for example, a vaporizer body that includes a battery and other hardware, and a cartridge or insert that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer may optionally be provided within a vaporizable material insert or cartridge (e.g., a part of the vaporizer that contains the vaporizable material) which can be refillable when empty, or disposable such that a new cartridge containing additional vaporizable material of a same or different type can be used. A vaporizer device can be a cartridge-using vaporizer device, a cartridge-less vaporizer device, or a multi-use vaporizer device capable of use with or without a cartridge. Some cartridge embodiments can include a vaporizable material insert. For example, embodiments of vaporizable material inserts can be at least partly made of a non-liquid vaporizable material. As such, some embodiments of the vaporizer device can be configured to receive a vaporizable material insert that is at least partly made of one or more vaporizable materials for heating and forming an inhalable aerosol, as will be described in greater detail below. In some embodiments, a vaporizer device can include a heating chamber or compartment (e.g., a vaporizable material insert receptacle) configured to receive a vaporizable material insert directly therein and heat the vaporizable material insert for forming an inhalable aerosol.

In some implementations, a vaporizer device can be configured for use with a liquid vaporizable material (for example, a carrier solution in which an active and/or inactive ingredient(s) are suspended or held in solution, or a liquid form of the vaporizable material itself) and/or a non-liquid vaporizable material (e.g., a paste, a wax, a gel, a solid, a plant material, and/or the like). A non-liquid vaporizable material can include a plant material that emits some part of the plant material as the vaporizable material (for example, some part of the plant material remains as waste after the material is vaporized for inhalation by a user) or optionally can be a solid form of the vaporizable material itself, such that all of the solid material can eventually be vaporized for inhalation. A liquid vaporizable material can likewise be capable of being completely vaporized, or can include some portion of the liquid material that remains after all of the material suitable for inhalation has been vaporized.

FIG. 1 depicts a block diagram illustrating an example of a vaporizer device 100 consistent with implementations of the current subject matter. Referring to FIG. 1, the vaporizer device 100 can include a power source 112 (for example, a battery, which can be a rechargeable battery), and a controller 104 (for example, a processor, circuitry, etc. capable of executing logic) for controlling delivery of heat from a heating element 150 to cause a vaporizable material 102 of a vaporizable material insert 122 to be converted from a condensed form (such as a solid, a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The heating element 150 can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the heating element 150 (e.g., a resistive heating element and/or the like) is configured to generate heat for vaporizing the vaporizable material 102 to generate an inhalable dose of the vaporizable material 102. As noted, the vaporizable material 102 may be a liquid or non-liquid (or combination of both liquid and non-liquid). For example, the heating element 150 may be wrapped around, positioned within, integrated into a bulk shape of, pressed into thermal contact with, or otherwise arranged to deliver heat to the vaporizable material 102 to be vaporized for subsequent inhalation by a user in a gas and/or a condensed (for example, aerosol particles or droplets) phase.

In some embodiments, the vaporizable material 102 may be a non-liquid vaporizable material including, for example, a solid-phase material (such as a gel, a wax, or the like) or plant material (e.g., tobacco leaves and/or parts of tobacco leaves). Where the vaporizable material 102 is a non-liquid vaporizable material, the heating element 150 can be part of, or otherwise incorporated into or in thermal contact with, the walls of a heating chamber or compartment (e.g., vaporizable material insert receptacle 118) into which the vaporizable material insert 122 is placed. Alternatively, the heating element 150 can be used to heat air passing through or past the vaporizable material insert 122, to cause convective heating of the vaporizable material 102 of the vaporizable material insert 122. In still other examples, the heating element 150 can be disposed in intimate contact with the vaporizable material 102 such that direct conductive heating of the vaporizable material 102 of the vaporizable material insert 122 occurs from within a mass of the vaporizable material 102, as opposed to only by conduction inward from walls of the heating chamber (e.g., an oven and/or the like). In some embodiments, the heating element 150 can be a part of the vaporizer body 110 (e.g., part of the durable or reusable part of the vaporizer 100), as shown in FIG. 1.

The heating element 150 can be activated in association with a user puffing (e.g., drawing, inhaling, etc.) on an end and/or mouthpiece of the vaporizer device 100 to cause air to flow from an air inlet, along an airflow path for assisting with forming an inhalable aerosol that can be delivered out through an air outlet in the mouthpiece. Incoming air moving along the airflow path moves over or through the heating element 150 and/or vaporizable material 102 where vaporizable material 102 in the gas phase is entrained into the air. The heating element 150 can be activated via the controller 104, which can optionally be a part of the vaporizer body 110 as discussed herein, causing current to pass from the power source 112 through a circuit including the heating element 150, which can be part of the vaporizer body 110. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece) for inhalation by a user.

Activation of the heating element 150 can be caused by automatic detection of a puff based on one or more signals generated by one or more sensor(s) 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of the heating element 150 of the vaporizer device 100 can depend on a number of factors, including an amount of electrical power delivered to the heating element 150 and/or a duty cycle at which the electrical power is delivered, conductive heat transfer to other parts of the vaporizer device 100 and/or to the environment, latent heat losses due to vaporization of the vaporizable material 102, and convective heat losses due to airflow (e.g., air moving across the heating element 150 when a user inhales on the vaporizer device 100). As noted herein, to reliably activate the heating element 150 or heat the heating element 150 to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element 150 can be activated in association with a user's puff, for example by automatic detection of the puff, or by the sensor 113 detecting a change (such as a pressure change) in the airflow path.

The sensor 113 can be positioned on or coupled to (e.g., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal resilient enough to separate an airflow path from other parts of the vaporizer device 100. The seal, which can be a gasket, can be configured to at least partially surround the sensor 113 such that connections of the sensor 113 to the internal circuitry of the vaporizer device 100 are separated from a part of the sensor 113 exposed to the airflow path. Such arrangements of the seal in the vaporizer device 100 can be helpful in mitigating against potentially disruptive impacts on vaporizer components resulting from interactions with environmental factors such as water in the vapor or liquid phases and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, errant portions of the vaporizable material 102, etc., in parts of the vaporizer device 100 where they can result in poor pressure signal, degradation of the sensor 113 or other components, and/or a shorter life of the vaporizer device 100. Leaks in the seal can also result in a user inhaling air that has passed over parts of the vaporizer device 100 containing, or constructed of, materials that may not be desirable to be inhaled.

In some implementations, the vaporizable material insert 122 can be configured for insertion in the vaporizable material insert receptacle 118, can have a non-circular cross section transverse to the axis along which the vaporizable material insert 122 is inserted into the vaporizable material insert receptacle 118. For example, the non-circular cross section can be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

When a user puffs on the vaporizer 100, air may pass between an outer surface of the vaporizable material insert 122 and an inner surface of a vaporizable material insert receptacle 118 of the vaporizer body 110. Air can then be drawn into and through at least a part of the vaporizer material insert 122 and out through an outlet of the vaporizable material insert 122 and/or vaporizer body 110 (e.g., a mouthpiece) for delivery of the inhalable aerosol to a user.

In some embodiments, the vaporizer device 100 can be configured to heat a non-liquid vaporizable material including, for example, a plant material (e.g., tobacco leaves), a plant material based product (e.g., reconstituted tobacco) and/or the like. For example, some embodiments of the vaporizer body 110 of the vaporizer device 100 can be configured to receive a vaporizable material insert 122 that is at least partly made out the non-liquid vaporizable material. For example, some embodiments of the vaporizable material insert 122 can include a housing (e.g., made out of a biodegradable material) that defines an inner chamber configured to contain vaporizable material (e.g., non-liquid vaporizable material). As such, some embodiments of the vaporizable material insert receptacle 118 can be configured to receive and heat the vaporizable material insert 122, such as for forming an inhalable aerosol. For example, an embodiment of the vaporizable material insert receptacle 118 can include a compartment that is configured for receiving and heating a variety of vaporizable material insert 122, as will be described below.

In some embodiments, the vaporizable material insert receptacle 118 can include all or part of the heating element 150 (e.g., a heating coil, etc.) that is configured to heat the vaporizable material insert 122 received in the vaporizable material insert receptacle 118, such as for forming the inhalable aerosol. Various vaporizable material insert embodiments are described herein for use with a variety of vaporizer bodies 110 for forming inhalable aerosol.

For example, some embodiments of the vaporizable material insert 122 can include a housing that forms a vaporization chamber configured to contain a vaporizable material and an airflow pathway. The airflow pathway can extend at least partly between an inlet and an outlet of the housing and allow a heated airflow to travel therealong. Various embodiments of the vaporizable material insert 122 are described herein that include one or more airflow pathway characteristics that change along the airflow pathway to allow a similar (e.g., the same or approximately the same) amount of heat transfer to be achieved between the heated airflow and the vaporizable material along the length of the airflow pathway. For example, the airflow pathway characteristics may enable a similar amount of heat to be transferred (e.g., per unit area of vaporizable material or per unit volume of vaporizable material) such that the vaporizable material is heated to the same or a similar temperature near the inlet and the outlet of the housing, despite heated air at the inlet having a higher temperature than heated air at the outlet.

For example, at least one airflow pathway characteristic (e.g., diameter, cross-section area, shape, length, etc.) can change along the airflow pathway to achieve a similar amount of heat transfer along the length of the airflow pathway. For example, by changing at least one airflow pathway characteristic, at least one airflow characteristic of the heated airflow can be changed, such as one or more of an airflow rate, an airflow resistance/pressure, and an airflow travel length. For example, an upstream portion of the airflow pathway (e.g., adjacent the inlet of the housing) can be sized and shaped to allow the heated airflow at higher temperatures to flow at a faster airflow rate and along a shorter length of the airflow pathway compared to the heated airflow at lower temperatures along a downstream portion of the airflow pathway (e.g., adjacent the outlet of the housing).

Such differences in airflow temperatures and airflow characteristics can achieve a similar amount of heat transfer along the upstream and downstream portions of the airflow pathway. Such similar amounts of heat transfer along the length of the airflow pathway can more evenly distribute heat through the vaporizable material of the vaporizable material insert 122, which can result in improved inhalable aerosol formation and efficient and effective consumption of the vaporizable material of the vaporizable material insert 122. Additionally, the vaporizable material insert 122 embodiments described herein can reduce or prevent overheating of the vaporizable material 102, as well as reduce or prevent waste of the vaporizable material 102.

In some embodiments, the vaporizable material insert 122 can include one or more airflow control features configured to control the variable airflow characteristics along the airflow pathway. For example, the airflow control feature can include a first part configured to cause a first airflow rate along the upstream section of the airflow pathway and a second part configured to cause a second airflow rate along the downstream portion to be greater. Additionally, the upstream section of the airflow pathway can have a shorter length compared to the downstream section of the airflow pathway. As discussed above, airflow characteristics and airflow temperatures (e.g., which effect a temperature gradient between the heated airflow and vaporizable material) can affect the amount of heat transferred between the heated airflow and the vaporizable material, such as to achieve similar amounts of heat transfer between the heated airflow and the vaporizable material along the length of the airflow pathway.

In some embodiments, the airflow control feature can include one or more vaporizable materials. For example, the vaporizable material of the airflow control feature can be contained in a substrate that is, at most, minimally air permeable. Additionally, in some embodiments, the airflow control feature can include the vaporizable material formed in a shape or configuration that assists with controlling the airflow along the airflow pathway. For example, the formed vaporizable material of the airflow control feature can define at least a part of the airflow pathway, which can include more than one pathway collectively forming the airflow pathway. The airflow pathway can include one or more of a variety of airflow pathway characteristics that assist with controlling one or more airflow characteristics of the heated airflow traveling therealong.

Figure 2A:
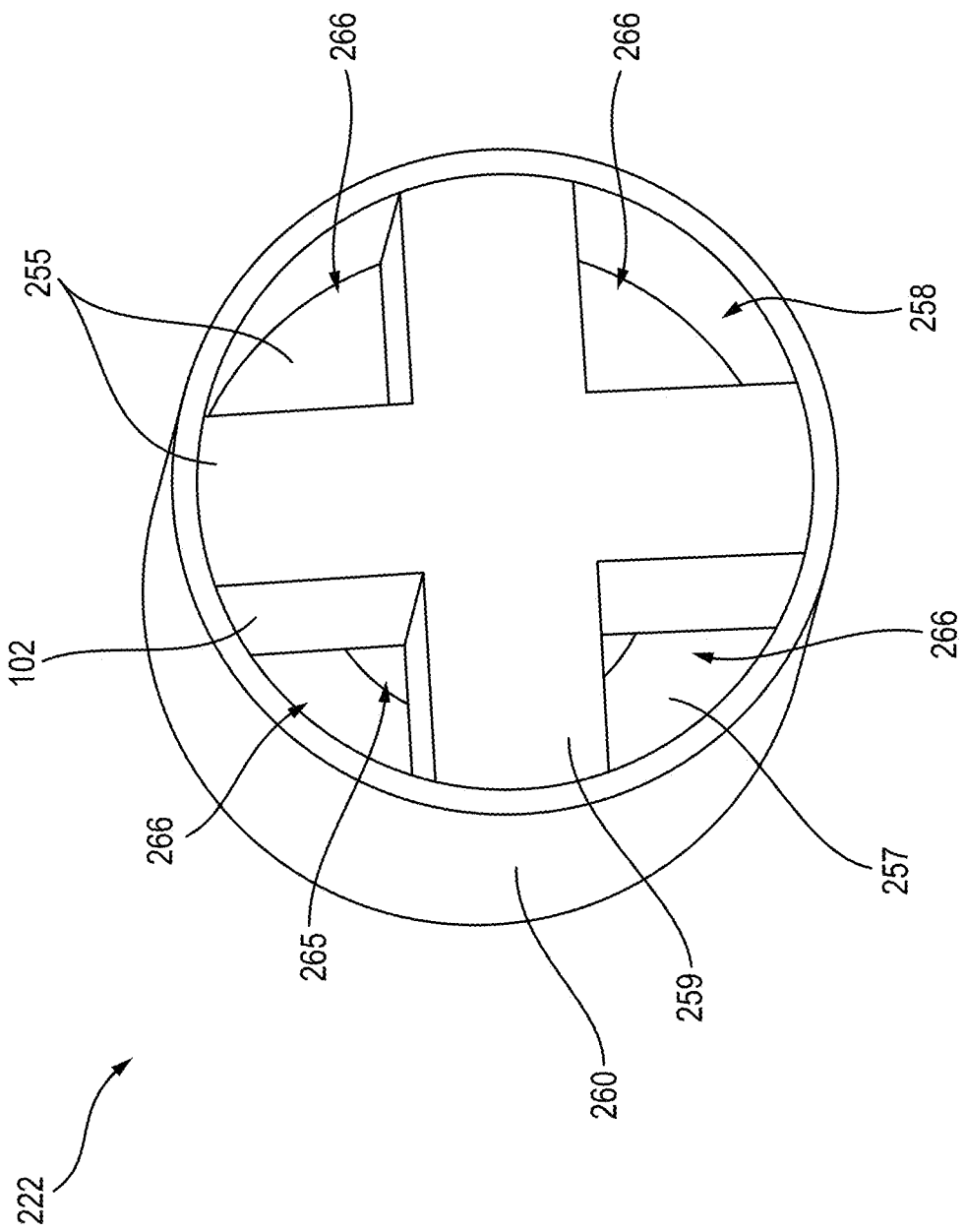
FIG. 2A illustrates a first embodiment of a vaporizable material insert that can be used with the vaporizer body of FIG. 1.
Figure 2B:
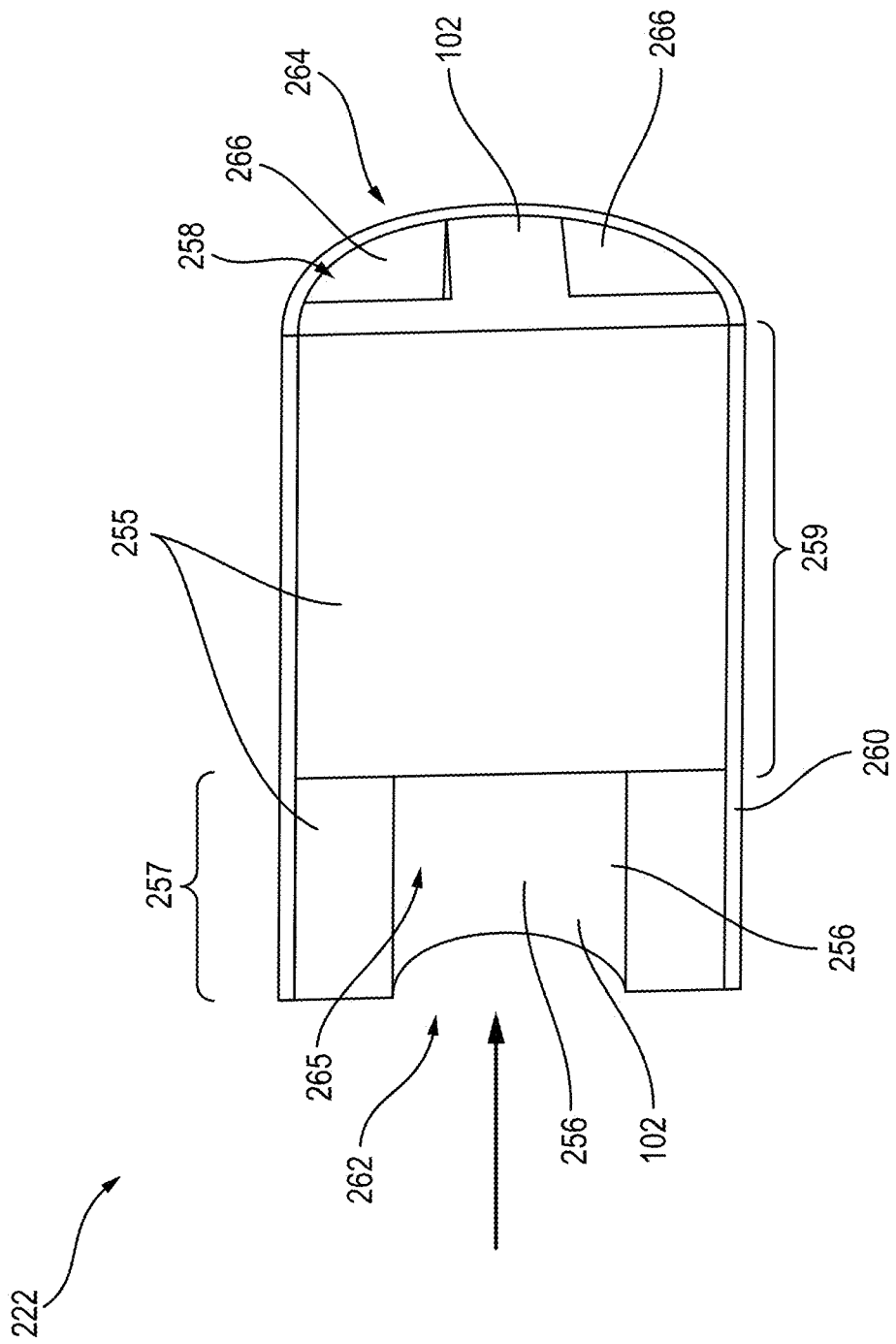
FIG. 2B illustrates a perspective view of the vaporizable material insert of FIG. 2A.

FIGS. 2A and 2B illustrate a first embodiment of the vaporizable material insert 222 that can be inserted in a receptacle (e.g., vaporizable material insert receptacle 118 of FIG. 1) of a vaporizer body 110 for heating and forming an inhalable aerosol. As shown in FIGS. 2A and 2B, the vaporizable material insert 222 can include an airflow control feature 255 at least partly contained in a housing 260. As shown in FIG. 2A, the housing 260 can be cylindrical, however, other housing shapes are within the scope of this disclosure. The housing 260 can form an inner chamber that extends between and inlet 262 and an outlet 264 of the housing 260. The airflow control feature 255 can be positioned within the inner chamber and extend at least partly between the inlet 262 and the outlet 264 of the housing 260. The housing 260 can be made out of a variety of materials, including one or more of a thermally conductive material, an insulative material, a biodegradable material, a vaporizable material, and a non-vaporizable material.

The airflow control feature 255 can be formed at least partly out of a non-liquid vaporizable material 102. The airflow control feature 255 can be shaped such that at least a part of an airflow pathway 265 extends through and/or along one or more sides of the airflow control feature 255. As such, at least part of the airflow pathway 265 can be formed by the airflow control feature 255, as shown in FIGS. 2A and 2B. For example, the airflow pathway 265 can extend between an inlet 262 and an outlet 264 of the housing 260, as well as extend along and/or through the airflow control feature 255. As will be described in greater detail below, heated airflow can travel along the airflow pathway 265 and heat the vaporizable material 102 comprising at least a part of the airflow control feature 255 for forming (e.g., via convection) an inhalable aerosol.

One or more airflow pathway characteristics of the airflow pathway 265 can change along the airflow pathway 265 thereby causing at least one airflow characteristic of the heated airflow to change while traveling along the airflow pathway 265. As discussed above, such change in airflow characteristics can affect the amounts of heat transfer between the heated airflow passing along the airflow pathway 265 and the vaporizable material 202 of the airflow control feature 255.

For example, a first part of the airflow control feature can define an upstream section of the airflow pathway 265 including a first diameter or cross-section area that results in a first amount of heat transfer between the heated airflow and the vaporizable material 102 along the first part of the airflow control feature 255. Furthermore, a second part of the airflow control feature can define a downstream section of the airflow pathway 265 including a second diameter or cross-section area that results in a second amount of heat transfer between the heated airflow and the vaporizable material 102 along the second part of the airflow control feature 255. In some embodiments, the first diameter or cross-section area of the first part can be greater than the second diameter or cross-section area of the second part and the airflow temperature traveling along the first part can be greater than the airflow temperature traveling along the second part. As such, the first amount of heat transfer along the first part can be similar (e.g., the same as or approximately equal) to the second amount of heat transferred (e.g., per unit of vaporizable material) along the second part. Additionally, in some embodiments, the first part and/or upstream section can include a shorter length compared to a length of the second part and/or downstream section, however, such lengths can be the same without departing from the scope of this disclosure. The airflow control feature 255 can include more than one parts that each include different airflow pathway characteristics (e.g., size, shape, diameter, cross-section area, length, etc.) for causing varying airflow characteristics (e.g., airflow rate, airflow resistance/pressure, airflow travel length) to achieve a similar amount of heat transfer between the heated airflow and vaporizable material along each part of the airflow control feature, as will be described in greater detail below.

As shown in FIG. 2B, the airflow control feature 255 can include a first part 257 that includes a ring shape extending along a first length of the housing 260. The ring shape of the first part 257 can include an inner-wall or diameter defining a cylindrical upstream section 256 of the airflow pathway 265. For example, the upstream section 256 can include a single airflow pathway that can have a same or similar inner-wall or diameter along the length of the upstream section 256. The outer diameter or outer-wall of the ring-shaped first portion 257 can mate with the housing 260, as shown in FIG. 2B.

As shown in FIG. 2A, the airflow control feature 255 can include a second part 259 that includes a cross shape extending along a second length of the housing 260. The cross-shape of the second part 259 of the airflow control feature 255 can form a downstream section 258 of the airflow pathway 265 including more than one secondary airflow pathways 266, such as four secondary airflow pathways 266, as shown in FIG. 2A. For example, each of the secondary airflow pathways 266 can be defined by an inner wall of the housing 260 and one or more sides or outer surfaces of the second part 259 of the airflow control feature 255.

The first part 257 and second part 259 of the airflow control feature 255 can each include one or more of a variety of shapes and sizes, including forming a variety of airflow pathways having a variety of airflow pathway characteristics. As such, various shaped airflow control features and airflow pathways having a variety of airflow pathway characteristics are within the scope of this disclosure for achieving the variable and desirable airflow characteristics along the airflow pathway, as discussed herein.

For example, the upstream section 256 of the airflow pathway 265 can include a diameter and a cross-sectional area that is greater than a diameter and cross-sectional area, respectively, associated with each secondary airflow pathway 266 of the downstream section 258. In some embodiments, the cross-sectional area of the upstream section 256 of the airflow pathway 265 is greater than the combined or total cross-sectional area of the secondary airflow pathways 266. Additionally, the upstream section 256 can include a shorter length compared to the downstream section 258. As such, one or more airflow characteristics (e.g., airflow rate and airflow travel length, etc.) along the upstream section 256 of the airflow pathway 265 can be different from one or more airflow characteristics along the secondary pathways 266. Such differences in airflow pathway characteristics, and thus airflow characteristics, can achieve a similar amount of heat transferred along the upstream section 256 and the downstream section 258.

The vaporizable material insert 222, when positioned in the vaporizable material insert receptacle 118, can be positioned and oriented such that the upstream section 256 of the airflow pathway 265 is positioned to first receive airflow heated by the heating element 150. As such, the first part 257 of the airflow control feature 255 can be positioned closer downstream from the heating element 150 compared to the second part 259 of the airflow control feature 255. As such, airflow having the highest temperatures can be introduced into and travel along the upstream section 256 of the airflow pathway 265 compared to the temperatures of the airflow that is introduced and travels along the downstream section 258 (e.g., due to heat loss along the upstream section 256). As such, the airflow control feature 255 can be configured to cause the heated airflow having a temperature within a higher temperature range to have a shorter amount of time to heat the vaporizable material along the upstream section 256, such as compared to the downstream section 258 where the heated airflow temperature is within a lower temperature range and can be allowed a longer amount of time to heat the vaporizable material along the downstream section 258. For example, the shorter amount of time can be a result of one or more of a faster airflow rate, a shorter airflow pathway length, and less airflow resistance/pressure along the upstream section 256. Additionally, the longer amount of time can be a result of one or more of a slower airflow rate, a longer airflow pathway length, and more airflow resistance/pressure along the downstream section 258.

The first part 257 and the second part 259 of the airflow control feature 255 can each include one or more of a variety of shapes and sizes, including forming a variety of airflow pathways each having a variety of airflow pathway characteristics. As such, airflow control features having a variety of shapes and sizes and airflow pathways having a variety of airflow pathway characteristics are within the scope of this disclosure for achieving similar heat transfer rates along the airflow pathway 265, as discussed herein. Additionally, the airflow control feature 255 can include two or more parts, such as two or more parts that each form or assist with forming airflow pathways having different airflow pathway characteristics. The airflow pathway 265 can also include more than two sections, such as two or more sections that each include different airflow pathway characteristics for achieving different airflow characteristics and similar amounts of heat transfer between the heated airflow (e.g., within different temperature ranges) and the vaporizable material along each section.

Figure 3:
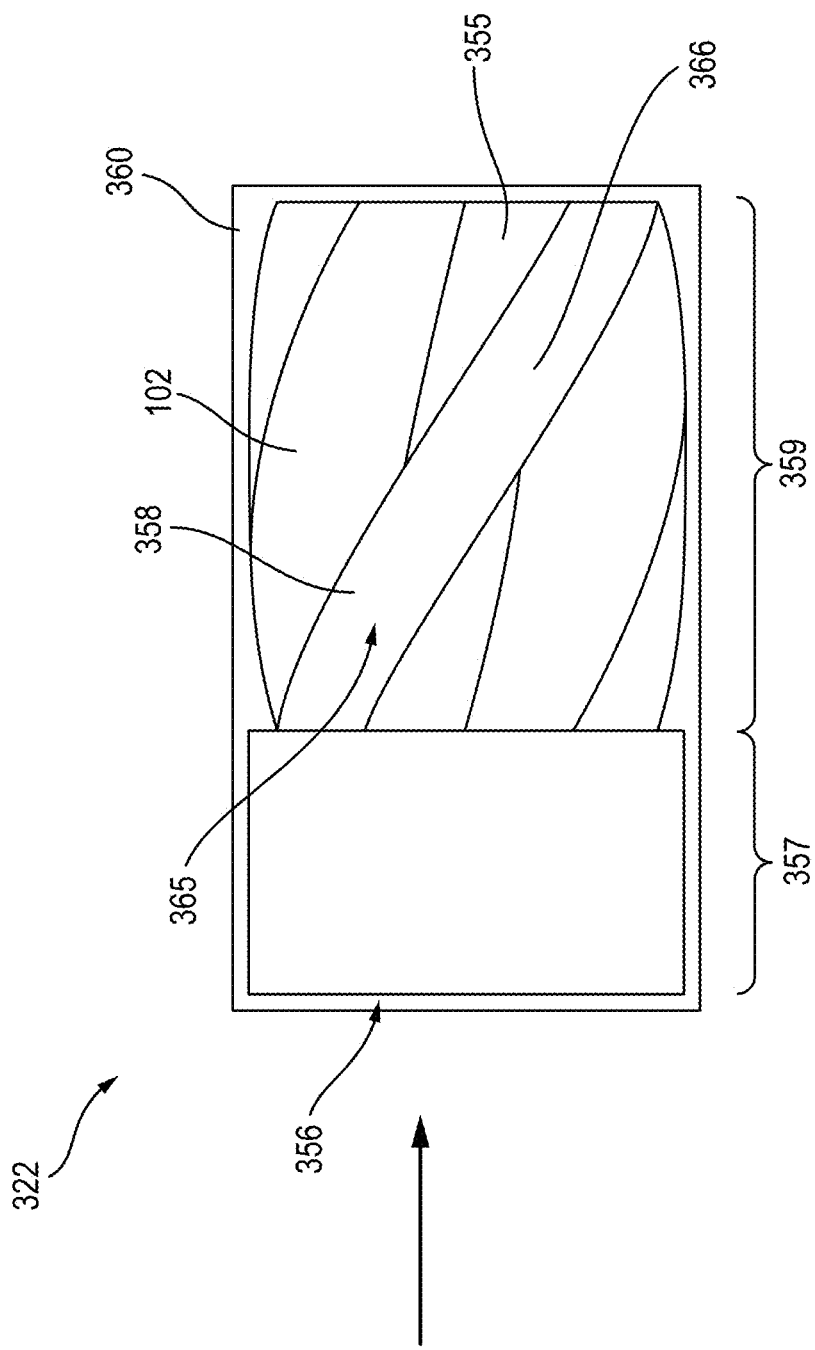
FIG. 3 illustrates a second embodiment of a vaporizable material insert.

FIG. 3 illustrates a second embodiment of the vaporizable material insert 322 including an airflow control feature 355 at least partly contained in a housing 360. As shown in FIG. 3, a first part 357 of the airflow control feature 355 can extend along a length of the housing 360 and include a vaporizable material 102 that can be formed in a ring shape. The ring-shaped first part 357 can include an inner diameter defining an upstream section 356 of the airflow pathway 365. The upstream section 356 can include a same or similar diameter across the length of the first part 357 of the airflow control feature 355.

As shown in FIG. 3, the airflow control feature 355 can include a second part 359 extending along another length of the housing 260. For example, the first part 357 can be shorter in length than the second part 359, as shown in FIG. 3. The second part 359 can also include vaporizable material 102 and can be formed in a twisted or helical shape defining a downstream section 358 of the airflow pathway 365. As shown in FIG. 3, the second part 359 can define or include one or more secondary airflow pathways 366 extending helically along the second part 359 (e.g., along a longitudinal axis of the second part 359). The airflow pathway 365 can include at least one airflow pathway characteristic that changes along the airflow pathway 365 such that a second airflow pathway characteristic along the downstream section 358 is different than a first airflow pathway characteristic along the upstream section 356. For example, the downstream section 358 can include a total cross-section area that is less than the cross-section area of the upstream section 356. Alternatively or in addition, each of the secondary airflow pathways 366 of the downstream section 358 can include a diameter that is smaller than the diameter of the upstream section 356 of the airflow pathway 365. As such, one or more airflow characteristics (e.g., airflow rate, airflow resistance/pressure, airflow travel length) along the helical secondary airflow pathways 366 can be different from one or more airflow characteristics of the airflow along the upstream section 356 of the airflow pathway 365.

Furthermore, the airflow characteristics of the heated airflow traveling along the helical secondary airflow pathways 366 can result in an amount of heat transfer between the heated airflow and the vaporizable material along the second part 359 of the airflow control feature that is similar to an amount of heat transfer achieved along the first part 357 of the airflow control feature 355. The upstream section 356 can be positioned adjacent or closest to the heating element 150 thereby encountering airflow having the highest temperatures. As such, the airflow control feature 355 can be configured to achieve a similar amount of heat transfer between the heated airflow and the vaporizable material along the length of the airflow pathway (e.g., extending between the inlet and outlet of the housing).

Figure 4:
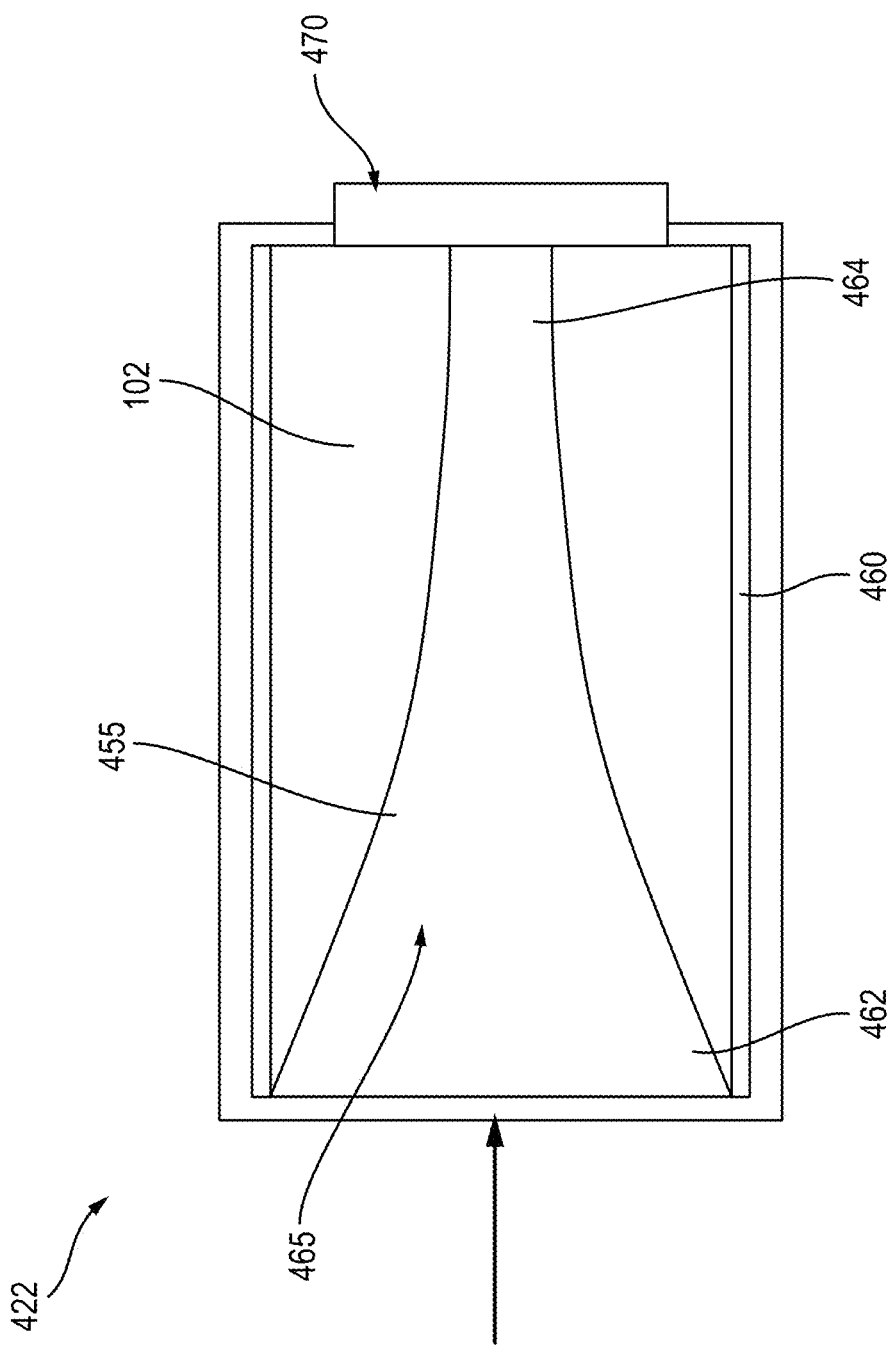
FIG. 4 illustrates a third embodiment of a vaporizable material insert.

FIG. 4 illustrates a third embodiment of the vaporizable material insert 422 including an airflow control feature 455 at least partly contained in a housing 460. As shown in FIG. 4, the airflow control feature 455 can include a vaporizable material 102 and form an airflow pathway 465 extending along a longitudinal axis of the airflow control feature 455. The airflow pathway 465 formed by the airflow control feature 455 can have a cylindrical or conical shape with an inner diameter that decreases (e.g., linearly, logarithmically) along the length of the airflow control feature 455. As shown in FIG. 4, the airflow pathway 465 can decrease in diameter or cross-sectional area along the length of the airflow pathway 465 in the direction of airflow along the airflow pathway 465. Such decreasing diameter along the airflow pathway 465 can cause one or more airflow characteristics of the heated airflow traveling along the airflow pathway 465 to vary therealong. The temperature of the heated airflow can also decrease as the heated airflow travels along the airflow pathway. As such, one or more of the airflow characteristics can change to accommodate a lower temperature of the heated airflow to achieve a similar amount of heat transfer between the heated airflow and the vaporizable material along the length of the airflow pathway 465.

For example, the amount of heat transfer between the heated airflow and the vaporizable material 102 of the airflow control feature 455 at an inlet end 462 (e.g., where a diameter of the airflow pathway 465 is largest) compared to an outlet end 464 (e.g., where a diameter of the airflow pathway 465 is smallest) can be similar. Furthermore, a rate of change of at least one airflow characteristic can change in relation/proportionate to a rate in change of at least one airflow characteristic, thereby achieving a similar amount of heat transfer between the heated airflow and the vaporizable material 102 along the airflow pathway 465. Such changes in airflow pathway characteristics, and thus changes in airflow characteristics, can achieve a similar amount of heat transfer between the heated airflow and vaporizable material along the airflow pathway 465 and/or airflow control feature 455. Other configurations for achieving uniform heat transfer along an airflow pathway are within the scope of this disclosure.

In some embodiments, the vaporizable material insert (e.g., any of the vaporizable material inserts 122, 222, 322, 422 described herein) may include a cooling filter 470 positioned adjacent the outlet of the housing (as shown, for example, in FIG. 4). The cooling filter 470 can cause airflow exiting the housing and airflow pathway to decrease in temperature prior to inhalation. For example, the cooling filter 470 may be formed of a porous substrate containing liquid vaporizable material and may be disposed adjacent the mouthpiece.

In some embodiments, the airflow control feature (e.g., any of the airflow control features 255, 355, 455 described herein) may include a substrate, such as a porous substrate (e.g., wick), saturated with liquid vaporizable material. In some embodiments, the airflow control feature may include a solid vaporizable material formed into a porous, moldable media, which can be saturated with a liquid vaporizable material, and/or a combination of both.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaporizable material insert for use with a vaporizer device to form an inhalable aerosol, the vaporizable material insert comprising:
    a housing including an inlet and an outlet;
    an airflow control feature comprising a vaporizable material, the airflow control feature extending between the inlet and the outlet of the housing; and
    an airflow pathway extending between the inlet and the outlet of the housing and at least partly formed by the airflow control feature, the airflow pathway allowing a heated airflow to travel therealong and including an upstream section and a downstream section, the upstream section including a first airflow pathway characteristic that controls a first airflow characteristic of the heated airflow for achieving a first amount of heat transfer between the heated airflow at a first temperature and the vaporizable material along the upstream section, the downstream section including a second airflow pathway characteristic that controls a second airflow characteristic of the heated airflow for achieving a second amount of heat transfer between the heated airflow at a second temperature and the vaporizable material along the downstream section, the first temperature being higher than the second temperature, and the first amount of heat transfer being approximately the same as the second amount of heat transfer.

2. The vaporizable material insert of claim 1, wherein the first airflow pathway characteristic and the second airflow pathway characteristic each comprise a diameter, a cross-section area, a shape, or a length of the upstream section and the downstream section, respectively, and wherein the first airflow pathway characteristic is different than the second airflow pathway characteristic.

3. The vaporizable material insert of claim 1, wherein the first airflow characteristic and the second airflow characteristic each comprise an airflow rate, an airflow resistance, an airflow pressure, or an airflow travel length, and wherein the first airflow characteristic is different than the second airflow characteristic.

4. The vaporizable material insert of claim 1, wherein the upstream section includes a single airflow pathway and the downstream section includes a plurality of secondary pathways, the single airflow pathway being in fluid communication with each secondary pathway included in the plurality of secondary pathways.

5. The vaporizable material insert of claim 4, wherein the plurality of secondary pathways extend in a helical shape along the airflow control feature.

6. The vaporizable material insert of claim 1, wherein the airflow pathway includes a diameter that decreases along the airflow pathway between the inlet and the outlet of the housing.

7. The vaporizable material insert of claim 1, wherein the upstream section of the airflow pathway is formed by a first part of the airflow control feature and the downstream section of the airflow pathway is formed by a second part of the airflow control feature, the first part having a different shape than the second part.

8. The vaporizable material insert of claim 7, wherein the first part forms a ring shape and the second part forms a cross shape.

9. The vaporizable material insert of claim 1, wherein the vaporizable material comprises a solid vaporizable material and/or the airflow control feature comprises a porous substrate containing liquid vaporizable material.

10. The vaporizable material insert of claim 1, further comprising a cooling filter positioned adjacent the outlet of the housing for reducing a temperature of the inhalable aerosol prior to inhalation by a user.

11. A system for generating an inhalable aerosol, the system comprising:
    a vaporizable material insert, comprising:
        a housing including an inlet and an outlet;

an airflow control feature comprising a vaporizable material, the airflow control feature extending between the inlet and the outlet of the housing; and an airflow pathway extending between the inlet and the outlet of the housing and at least partly formed by the airflow control feature, the airflow pathway allowing a heated airflow to travel therealong and including an upstream section and a downstream section, the upstream section including a first airflow pathway characteristic that controls a first airflow characteristic of the heated airflow for achieving a first amount of heat transfer between the heated airflow at a first temperature and the vaporizable material along the upstream section, the downstream section including a second airflow pathway characteristic that controls a second airflow characteristic of the heated airflow for achieving a second amount of heat transfer between the heated airflow at a second temperature and the vaporizable material along the downstream section, the first temperature being higher than the second temperature, and the first amount of heat transfer being approximately the same as the second amount of heat transfer; and a vaporizer device comprising:

a vaporizable material insert receptacle configured to receive the vaporizable material insert; and a heating element configured to heat airflow upstream from the vaporizable material insert for allowing heated airflow to travel along the airflow pathway of the vaporizable material insert and generate the inhalable aerosol.

12. The system of claim 11, wherein the first airflow pathway characteristic and the second airflow pathway characteristic each comprise a diameter, a cross-section area, a shape, or a length of the upstream section and the downstream section, respectively, and wherein the first airflow pathway characteristic is different than the second airflow pathway characteristic.

13. The system of claim 11, wherein the first airflow characteristic and the second airflow characteristic each comprise an airflow rate, an airflow resistance, an airflow pressure, or an airflow travel length, and wherein the first airflow characteristic is different than the second airflow characteristic.

14. The system of claim 11, wherein the upstream section includes a single airflow pathway and the downstream section includes a plurality of secondary pathways, the single airflow pathway being in fluid communication with each secondary pathway included in the plurality of secondary pathways.

15. The system of claim 14, wherein the plurality of secondary pathways extend in a helical shape along the airflow control feature.

16. The system of claim 11, wherein the airflow pathway includes a diameter that decreases along the airflow pathway between the inlet and the outlet of the housing.

17. The system of claim 11, wherein the upstream section of the airflow pathway is formed by a first part of the airflow control feature and the downstream section of the airflow pathway is formed by a second part of the airflow control feature, the first part having a different shape than the second part.

18. The system of claim 17, wherein the first part forms a ring shape and the second part forms a cross shape.

19. The system of claim 11, wherein the vaporizable material comprises a solid vaporizable material and/or the airflow control feature comprises a porous substrate containing liquid vaporizable material.

20. The system of claim 11, wherein the vaporizable material insert further comprises a cooling filter positioned adjacent the outlet of the housing for reducing a temperature of the inhalable aerosol prior to inhalation by a user.

* * * * *